United States Patent [19]

Wick

[11] Patent Number: 5,109,077
[45] Date of Patent: Apr. 28, 1992

[54] BIOCOMPATIBLE POLYURETHANE

[75] Inventor: Gerhard Wick, Obernburg, Fed. Rep. of Germany

[73] Assignee: Azko NV, Arnheim, Netherlands

[21] Appl. No.: 479,350

[22] Filed: Feb. 13, 1990

Related U.S. Application Data

[63] Continuation of Ser. No. 98,739, Sep. 15, 1987, abandoned, which is a continuation of Ser. No. 612,441, May 21, 1984, abandoned.

Foreign Application Priority Data

May 21, 1983 [DE] Fed. Rep. of Germany ....... 3318730

[51] Int. Cl.⁵ .................. C08L 69/00; C08L 75/04
[52] U.S. Cl. .................... 525/467; 525/453; 528/65
[58] Field of Search .................. 525/453, 467; 528/65

[56] References Cited

U.S. PATENT DOCUMENTS

| | | | |
|---|---|---|---|
| 3,544,524 | 12/1970 | Müller | 525/467 |
| 3,764,457 | 10/1973 | Chang et al. | 525/467 |
| 3,870,683 | 3/1975 | Freure et al. | 525/453 |
| 4,113,705 | 9/1978 | Bock et al. | 525/467 |
| 4,476,293 | 10/1984 | Robinson | 525/467 |
| 4,637,909 | 1/1972 | Bonin | 525/467 |
| 4,816,529 | 3/1989 | Harris | 525/453 |
| 4,861,909 | 8/1989 | Harris | 525/453 |
| 5,001,208 | 3/1991 | Ross et al. | 528/65 |

Primary Examiner—Ana L. Carrillo
Attorney, Agent, or Firm—Michael J. Striker

[57] ABSTRACT

A process is disclosed for the production of bio-compatible polyurethane, proceeding from cyclo aliphatic diisocyanate and macrodiol, which are reacted into a pre-adduct that is then chain lengthened with a mixture of the lower-molecular diol and a macrodiol. The so-obtained polyurethane displays high resistance in human and animal bodies and is suitable for the manufacture of catheters, blood pumps, heart valves, as well as bio-compatible lacquers and coatings.

18 Claims, No Drawings

BIOCOMPATIBLE POLYURETHANE

This is a continuation of application Ser. No. 098,739 filed Sep. 15, 1987, which in turn is a continuation under Rule 1.60 of Ser. No. 612,441, filed May 21, 1984, both now abandoned.

BACKGROUND OF THE INVENTION

The invention is based upon bio-compatible polyurethane based upon cyclo aliphatic diisocyanates, aliphatic and/or cyclo aliphatic macrodiols and lower-molecular aliphatic and/or cyclo aliphatic diols, which if necessary are dissolved in a solvent, the process for the production thereof as well as the employment of these polyurethanes for the production of bio-compatible shaped bodies.

Polyurethanes have been known for a long time and are prepared according to the most different techniques. Thus, for example, a macrodiol can be reacted with diisocyanate into a pre-adduct, the pre-adduct then being further reacted with one or more lower-molecular diols for the purpose of chain lengthening. It is also to react diisocyanate, macrodiol and chain lengthener simultaneously according to the so-called one pot process.

A distinguishing factor characteristic of polyurethane as compared to other synthetic materials is that they are relatively bio-compatible, i.e., they are extensively accepted by human or animal bodies, thus being compatible with the body and in particular displaying blood- and tissue-compatibility.

The heretofore bio-compatible polyurethane display, however, a series of disadvantages. On the one hand, they become disadvantageously influenced by hydrolytical factors within a more or less brief period of time whereby the mechanical characteristics, such as tensile strength, elongation and elasticity are affected, many polyurethanes thus indeed being completely decomposed within the course of time.

The above described deficiencies are also disadvantageously perceptible with bio-compatible shaped bodies if they are composed of such polyurethanes.

It is also known to manufacture so-called vessel prostheses in the form of tubing or thin tubules by means of the spinning of fibers from polymer solutions, transportation and laying down of fibers onto the rod or stick-shaped substrate so as to provide a fleece.

A technique is thus described in European patent 5035, for example, whereby the polymer solution is spun by means of the so-called electrostatic spinning process. An entire series of polymers is recommended as spinning solution for the manufacture of these plastic vessel prostheses, such as polyamide, polyacrylonitrile, polyurethane. In addition, polymers such as polytetrafluorethylene which can be worked up as a dispersion should be employable according to the teachings of this European patent.

A further process for the preparation of such vessel prostheses is described in DE-OS 28 06 037, according to which the prostheses are formed by means of fiber or filament spraying from a polymer solution. The reference sets forth in its Examples various market-accessible polyurethanes. Also with these techniques the above described disadvantages of polyurethane are observed.

When also the technology for the production of vessel prostheses has already been developed according to the most different techniques such as e.g., through preparation of fibers or filaments and a laying down thereof onto a rod or stick into a fleece or by means of extrusion of a solution, the behavior of the synthetic vessels in human or animal bodies depends not only upon the techniques with which the working up of the polymers have been implemented, but even the polymer itself plays a completely distinguishing role, moreover its chemical construction and in particular the manner of the preparation thereof.

SUMMARY OF THE INVENTION

There exists therefore, still a need for polyurethanes which of simple and advantageous type and manner can be worked up into bio-compatible shaped bodies that are economically accessible and which are distinguished particularly by means of a high degree of permanence, i.e., durability in human or animal bodies.

It is therefore an object according to the present invention to make available such polyurethanes.

This object is attained by means of a process of production for bio-compatible polyurethane if necessary dissolved in an organic solvent, by means of reaction of diisocyanates and diols into a pre-adduct and chain-lengthening of the pre-adduct with a mixture of chain lengtheners.

In particular, the present technique is characterized by reacting a cyclo aliphatic diisocyanate and an aliphatic and/or cyclo aliphatic macrodiol, in the absence of a solvent into a pre-adduct, employing 3 to 22 mol diisocyanate per mol macrodiol, the obtained pre-adduct then being lengthened in its chain with a mixture of lower-molecular aliphatic and/or cyclo aliphatic diol and an aliphatic and/or cyclo aliphatic macrodiol, if necessary in solution, selecting as pre-adduct in a molar ratio NCO groups to OH groups of the chain lengthener mixture 1.15:1 to 1.01:1.

Particularly advantageous method parameters include that 6.5 to 8 mol diisocyanate are employed per mol macrodiol;

a pre-adduct is adjusted in a molar ratio NCO group to OH group of the chain lengthener mixture from 1.07:1 to 1.04:1;

polytetramethyleneglycol having an average molecular weight $N_w$ from 600 to 2000 is employed for the construction of the pre-adduct while a mixture of butane diol-(1,2) and polytetramethyleneglycol is employed for the chain lengthening;

polycarbonate is used as macrodiol;

4,4'-dicyclohexylmethanediisocyanate is employed as cyclo aliphatic diisocyanate;

cyclohexanediisocyanate-(1,4) is employed as cylco aliphatic diisocyanate;

4,4'-dicyclohexylmethane diisocyanate in mixture with cyclohexanediisocyanate is employed as cyclo aliphatic diisocyanate;

the pre-adduct and chain lengthener mixture is reacted at a weight ratio from 30:70 to 70:30;

more particularly, a weight ratio from 60:40 to 40:60;

the polyurethane dissolved in an organic solvent is selected having a viscosity from 0.2 to 7.5 pA.s; and the employed solvent is selected from one or more of the following compounds: methylenchloride, acetone, chloroform, trichlorethylene, tetrahydrofuran, dioxan, n-propanol, cyclohexanol, dimethylformamide, dimethylacetamide.

Particularly advantageous specifics for the polyurethane according the present invention include a use for the production of bio-compatible shaped bodies;

catheters, so-called venous and fast catheters as well as peritoneal catheters by means of extrusion;

tubing by means of extrusion;

manufacture of blood pumps by means of the casting of a solvent-free and reactive mixture of pre-adduct and chain lengthener for a hardening into a cast shape;

manufacture of blood sacs (i.e., containers) by means of extrusion or from solution;

manufacture of heart valves;

manufacture of bio-compatible lacquers and coatings; and manufacture of vessel prostheses by means of pressing of polyurethane solution through nozzles and shaping into fibers or filaments along with evaporation of the solvent and placing of the filaments on a rod or otherwise shaped support into a filament fleece.

For performance of the method according to the present invention an aliphatic and/or cyclo aliphatic macrodiol is initially reacted with a cyclo aliphatic diisocyanate in the absence of a solvent into apreadduct. The cyclo aliphatic diisocyanate is employed in excess relative to the macrodiol in order that there be present after the reaction and in addition to addition products still free diisocyanate.

Suitable for construction of the pre-adduct according to the present invention as aliphatic and/or cyclo aliphatic macrodiol are: polyetherglycols, polycarbonates, e.g., polyhexamethylene carbonate (Desmophen 2020 of the firm Bayer A. G. Leverkusen, Federal Republic of Germany) and other two OH-terminal group displaying polymers.

According to a particularly advantageous embodiment of the method according to the present invention, polytetramethyleneglycol having an average molecular weight $M_w$ from 600 to about 2000 are employed.

With regard to the cyclo aliphatic diisocyanate, it is preferable to employ 4,4'-dicyclohexylmethanediisocyanate, particularly isomer mixtures thereof, such as are obtainable commercially, cyclohexane diisocyanate-1,4 in trans- and cis-form, as well as mixture of trans- and cis-isomers. Also suitable are mixtures of 4,4'-dicyclohexylmethanediisocyanate; and cyclohexanediisocyanate-(1,4).

The use of a catalyst is usually not necessary for the production of the pre-adduct.

The pre-adduct is then chain lengthened with a mixture of chain lengtheners containing a lower-molecular aliphatic and/or cyclo aliphatic diol preferably having 2 to 8 carbon atoms and an aliphatic and/or cyclo aliphatic macrodiol.

Suitable and particular as chain lengthener is a mixture of butandiol-(1,4) and polytetramethyleneglycol having an average weight $M_w$ equalling 600 to 2000.

The designation aliphatic and/or cyclo aliphatic diols respectively macrodiols, is understood within the sense of the present invention to mean diols which contain only aliphatic only cycloaliphatic or not only aliphatic but also cyclo aliphatic groups. To be employed as macrodiol and lower molecular diol are aliphatic or cyclo aliphatic compounds since these in known manner display a low chemical reactivity and outstanding light resistance, e.g., in comparison to the aromates, and in an employment for medical-related utility low chemical reactivity values must be the case.

In addition to the preferred butandiol, also following diols among others can be employed in the chain-lengthening mixture: neopentylglycol, ethylenglycol, propandiol-(1,3) and hexandiol-(1,6).

Preferably, the chain lengthening is effected in the presence of a catalyst. Suitable catalysts include in particular organotin compounds such as dibutyltinlaurate, dibutyltindioctoate, and the like.

The chain lengthening can similarly be performed without the presence of a solvent. It is also possible to work in the presence of one or more solvents. Belonging to the most preferred group thereof are e.g., dimethylacetamide, or dimethylformamide. When working without solvent it is favorable in order to obtain an advantageous premixing of the pre-adduct and the chain lengthener mixture to mix initially both components in a weight ratio from 70:30 to 30:70, preferably 60:40 to 40:60, and most particularly 55:45 to 45:55.

After the pre-mixing an outgassing is performed followed by allowing reaction to take place. The reacting out can be performed at higher temperatures, e.g., at 80° C. This operation, also known as a hardening out, can occur within a course of up to three or more days.

The obtained polyurethane can then be worked into granulate form and be stored for an optionally long period.

In the event that the chain lengthening is performed in solvent, the polyurethane can be separated by means of precipitation in water and then dried.

On the other hand, the polyurethane present in the solution can be left in solution and prepared into an immediately workable solution of suitable viscosity by means of addition of further solvent.

The polyurethane prepared according to the present invention can be worked up according to known techniques into bio-compatible shaped bodies such as vessel prostheses, catheters, blood pumps, heart valves and other blood conveying cavity organs such as tubing, otoplastics, protective skins for probes and the like. Thus, the polyurethane can be shaped by means of extruding its melt.

According to one particular casting technique, the pre-adduct is cast into already prepared molds after mixing with the appropriate amount of chain lengthener and outgassing. After hardening, form-faithful impressions are obtained, which can be withdrawn very easily from teflon or silicon molds. A preferred utility for objects prepared according to this technique is blood pumps and otoplastics (ear sculptings).

For the production of lacquers or bio-compatible coatings, the polyurethane according to the present invention is dissolved in solvent to provide, preferably, about 5% by weight solution at room temperature, which is then used to coat probes.

For the working up into vessel prostheses the polyurethane is preferably employed dissolved and worked up in known manner into such vessel prosthesis, whereby preferably a solution is used for the preparation of fibers or filaments which are then laid onto a support in the form of a fleece. Such techniques are described for example in EP-PS5035 and in U.S. Pat. No. 4,004,404. The methods disclosed in these references concern a technique with which the filaments are manufactured through utilization of an electrostatical field.

A further suitable, preferred technique for the manufacture of such vessel prostheses is described in DE-OS 28 06 030.

4. The process according to claim 1, wherein said reacting to form said pre-adduct is performed with 6.5 to 8 Mol diisocyanate per Mol polycarbonate polymer.

5. The process according to claim 1, wherein the molar ratio of the NCO-groups of said pre-adduct to the OH-groups of said chain-lengthening mixture is from 1.07:1 to 1.04:1.

6. The process according to claim 1, wherein said reacting to form said pre-adduct is effected with polyhexamethylenecarbonate as said polycarbonate polymer and said chain-lengthening is effected with butanediol-(1,4) as said low molecular aliphatic diol.

7. The process according to claim 1, wherein said cycloaliphatic diisocyanate is 4,4'-dicyclohexylmethane diisocyanate.

8. The process according to claim 1, wherein said cycloaliphatic diisocyanate is cyclohexane diisocyanate-(1,4).

9. The process according to claim 1, wherein said cycloaliphatic diisocyanate is a mixture of 4,4'-dicyclohexylmethane diisocyanate and cyclohexane diisocyanate.

10. The process according to claim 1, wherein said pre-adduct and said chain-lengthening mixture are provided in a weight ratio of from 30:70 to 70:30.

11. The process according to claim 1, wherein said pre-adduct and said chain-lengthening mixture are provided in a weight ratio of from 60:40 to 40:60.

12. The process according to claim 1, wherein said chain-lengthening is performed in solution and further comprising adjusting a viscosity of the polyurethane produced as final product to from 0.2 to 7.5 Pa's.

13. The process according to claim 1, wherein said chain-lengthening is performed in solution, employing an organic solvent selected from the group consisting of methylene chloride, acetone, chloroform, trichloroethylene, tetrahydrofuran, dioxan, n-propanol, cyclohexanol, dimethylformamide and dimethylacetamide.

14. The process according to claim 1, wherein said chain-lengthening is performed in solution; and further comprising allowing said polyurethane to separate out by means of precipitation in water.

15. The process according to claim 1, further comprising forming a solution of said pre-adduct and said chain lengthening mixture of a certain viscosity and adding additional solvent to said solution to change said viscosity.

16. The process according to claim 1, in which said polycarbonate polymer used to make said pre-adduct is the same as said other polycarbonate polymer used in said step of said chain-lengthening.

17. The process according to claim 16, in which said polycarbonate polymer comprises polyhexamethylenecarbonate.

18. Process for production of biocompatible polyurethane, comprising:
  a. reacting cycloaliphatic diisocyanate and an aliphatic or cycloaliphatic polycarbonate polymer, using excess of diisocyanate, to form a pre-adduct, said reacting being performed in the absence of solvent, and,
  b. chain-lengthening said pre-adduct with a mixture of low molecular weight aliphatic or cycloaliphatic diol having from 2 to 8 carbon atoms and another aliphatic or cycloaliphatic polycarbonate polymer, with molar excess of said diisocynate to said polycarbonate polymer,
  said pre-adduct employed in a molar ratio excess of NCO-groups to OH-groups of said chain lengthening mixture.

* * * * *

It was completely surprising that the polyurethane according to the present invention can be worked up in this manner into vessel prostheses which once implanted display practically no loss of their mechanical and physical characteristics, even after periods of twelve and more months. It is further surprising that in connection with the working up of these filaments according to the so-called filament spray techniques, as are disclosed e.g., in DE-OS 28 06 030, the clot formation can be reduced considerably. The designation clot- The polyurethane can be worked up in the form of a 5% by weight solution of a solvent mixture composed of equal parts acetone, methylenechloride and chloroform by means of filament spraying according to the teachings of DE-OS 28 06 030.

EXAMPLES 2-8

In analogus manner of operation polyurethanes are prepared from starting materials and as set forth in the following Table:

TABLE

| EXAMPLE | DIISOCYANATE | MACRODIOL | LOWER MOLECULAR DIOL | MACRODIOL |
|---|---|---|---|---|
| 2 | 11 Val DCHMDI | 1.5 Val PTG 650 | 4.5 Val Butandiol-(1,4) | 4.5 Val PTG 650 |
| 3 | 11 Val | 0.75 Val PTG 650+<br>0.75 Val PTG 1000 | 4.5 Val Butandiol-(1,4) | 2.25 Val PTG 650+<br>2.25 Val PTG 1000 |
| 4 | 12.5 Val DCHMDI | 1.2 Val PTG 1000+<br>0.6 Val PTG 2000 | 5.6 Val Butandiol-(1,4) | 3.8 Val PTG 650+<br>1.3 Val PTG 1000 |
| 5 | 9.7 Val DCHMDI +<br>1.3 Val CHDI tr | 1.5 Val PTG 1000 | 4.5 Val Butandiol-(1,4) | 4.5 Val PTG 1000 |
| 6 | 0.18 Val CHDI cis | 0.025 Val PTG 1000 | 0.135 Val NPG | 0.02 Val PTG 1000 |
| 7 | 11 Val DCHMDI | 1 Val PTG 1000+<br>0.5 Val Baysilon-OF<br>OH 502 | 4.5 Val Butandiol-(1,4) | 4.5 Val PTG 1000 |
| 8 | 11 Val DCHMDI | 1.5 Val Desmophen 2020 | 4.5 Val Butandiol-(1,4) | 4.5 Val Desmophen 2020 |

DCHMDI = 4.4'-dicyclohexylmethandiisocyanate, CHDI = cyclohexandiisocyanate-(1,4), tr = trans, PTG = polytetramethylenglycol, Desmophen 2020 = polyhexamethylencarbonate, NPG = neopentylglycol, Baysilon-OF OH 502 = OH-terminal group displaying dimethylsiloxane of Bayer AG
Val = equivalent formation or non-filament-like clump formation is to be understood as embracing thick places on the fleece obtained at the rod or otherwise support, which presumably may be attributed that based upon differences in viscosity within the spinning solution instigate a differential evaporation at the forming filaments whereby these clots or clumps can occur.

The novel features which are considered characteristic for the invention are set forth in particular in the appended claims. The invention itself, however, both as to its construction and its method of operation, together with additional objects and advantages thereof, will be best understood from the following description of specific embodiments.

EXAMPLE 1

A three-neck flask, provided with stirrer, nitrogen conveyance and cooler with discharge tube is filled with 11 VAL 4,4'-dicyclohexylmethandiisocyanate and 1.5 VAL water-free polytetramethyleneglycol $M_w$ − 1000, followed by three hours' duration heating at 120° C. under fixed stirring. The addition reaction for manufacture of the pre-adduct is effected until a theoretically calculated isocyanate content of 18.2% by weight is obtained. Meanwhile, for production of the chain lengthener, 4.5 VAL water-free butandiol-(1,4) and 4.5 VAL water-free polytetramethyleneglycol $M_w$ − 1000 are mixed together under stirring in another closed vessel with a tin catalyst (5 mg dibutyltindilaurate/100 g total amount of chain lengthener). When necessary, this pre-mixing is performed under mild heating of about 50° C. For the manufacture of the polyurethane, 46.75 g pre-adduct is stirred in with 53.25 g chain lengthener at a mixing temperature of 50° C. This mixture is outgassed and then cast into a hardening out mold. After a hardening period of three days at 80° C. a relative viscosity of 3.056 is measured (1% by weight in dimethylformamide). The Shore A-hardness of the polyurethane comes to 80, the softening range lying at about 125° C. and the melting range is approximately 185° C. The polyurethane is transparent and colorless.

It will be understood that each of the elements described above, or two or more together, will also find a useful application in other types of synthetic articles differing from the types described above.

While the invention has been illustrated and described as embodied in bio-compatible polyurethane, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. Process for production of biocompatible polyurethane, comprising the steps of:
   a. reacting cycloaliphatic diisocyanate and an aliphatic or cycloaliphatic polycarbonate polymer, using molar excess of diisocyanate, to form a pre-adduct having NCO groups, said reacting being performed in the absence of solvent, and
   b. chain lengthening said pre-adduct with a chain lengthening mixture of low molecular aliphatic or cycloaliphatic diol having from 2 to 8 carbon atoms and another aliphatic or cycloaliphatic polycarbonate polymer to form said polyurethane, said mixture having OH groups.

2. The process according to claim 1, wherein said reacting to form said pre-adduct is performed with 3 to 22 Mol diisocyanate per Mol polycarbonate polymer.

3. The process according to claim 1, wherein the molar ratio of the NCO-groups of said pre-adduct to the OH-groups of said chain-lengthening mixture is from 1.15:1 to 1.01:1.